United States Patent [19]

Vieillefosse et al.

[11] Patent Number: 5,428,450
[45] Date of Patent: Jun. 27, 1995

[54] METHOD AND APPARATUS FOR DETERMINING THE COLOR OF AN OBJECT THAT IS TRANSPARENT, DIFFUSING, AND ABSORBENT, SUCH AS A TOOTH, IN PARTICULAR

[75] Inventors: Michel Vieillefosse, Aix en Provence; Olivier Belle, Rousset, both of France

[73] Assignee: Bertin & Cie, France

[21] Appl. No.: 170,019

[22] Filed: Dec. 20, 1993

[30] Foreign Application Priority Data

Dec. 22, 1992 [FR] France ................... 92 15452

[51] Int. Cl.⁶ ..................... G01N 21/27; G01J 3/51
[52] U.S. Cl. ..................... 356/405; 356/407; 356/419
[58] Field of Search .............. 356/405, 406, 407, 418, 356/419

[56] References Cited

U.S. PATENT DOCUMENTS

| | | |
|---|---|---|
| 3,383,979 | 5/1968 | Gibson . |
| 3,526,777 | 9/1970 | Robinson ............ 250/237 |
| 4,022,534 | 5/1977 | Kishner . |
| 4,029,391 | 6/1977 | French ............ 356/418 |
| 4,082,458 | 4/1978 | Fukui et al. ............ 356/418 |

FOREIGN PATENT DOCUMENTS

| | | |
|---|---|---|
| 209860 | 1/1987 | European Pat. Off. . |
| 279191 | 8/1988 | European Pat. Off. . |
| 367647 | 5/1990 | European Pat. Off. . |
| 1902101 | 1/1971 | Germany . |
| 3406175 | 8/1985 | Germany . |

*Primary Examiner*—Vincent P. McGraw
*Attorney, Agent, or Firm*—Bell, Seltzer, Park & Gibson

[57] ABSTRACT

A method and apparatus for determining the color of an object which is transparent, diffusing, and absorbent, by illuminating an area of the object by means of a diffuse light flux that is substantially uniform and isotropic, by picking up the light backscattered by a small fraction of the illuminated area of the object by means of an optical system that comprises achromatic doublets and both infrared and ultraviolet filters, together with a diaphragm, and spectrally analyzing said light by means of interference filters and photodetectors. The invention is particularly suitable for determining the color of teeth in the mouth.

18 Claims, 2 Drawing Sheets

METHOD AND APPARATUS FOR DETERMINING THE COLOR OF AN OBJECT THAT IS TRANSPARENT, DIFFUSING, AND ABSORBENT, SUCH AS A TOOTH, IN PARTICULAR

FIELD OF THE INVENTION

The invention relates to a method and apparatus for determining the color of an object that is transparent, diffusing, and absorbent, such as a tooth in the mouth, in particular.

BACKGROUND OF THE INVENTION

Proposals have already been made to perform such color determination by illuminating the surface of the object or of the tooth with polychromatic light flux, by picking up the light backscattered by said object or said tooth, and by analyzing the spectrum of the light picked up, in particular to determine the spectral reflectance of the object or of the tooth.

In theory, knowledge of such spectral reflectance makes it possible without risk of error and in particular without risk of metamerism to determine the color that should be given to a dental prosthesis that is implanted next to the tooth on which the measurement has been performed, or the color to be given to a series of objects reproducing the object on which the measurements have been performed.

Nevertheless, in practice, it turns out that there are several difficulties in implementing that known technique which lead to relatively large color differences between a tooth in the mouth and a dental prosthesis between an object and the reproductions of said object.

These differences are due, firstly, to the sensitivity characteristics of the human eye, and secondly to the way in which teeth or objects that are to be reproduced are transparent, diffusing, and absorbent to greater or lesser extents.

These difficulties are further aggravated when manufacturing dental prosthesis since natural teeth are generally more transparent than artificial teeth.

To solve these problems, the Applicant has already developed a method of determining the color of a transparent or translucent object, e.g. a tooth in the mouth, as disclosed and protected by U.S. patent application Ser. No. 07/991201 filed on Dec. 15, 1992 the contents of which is incorporated herein by reference.

In summary, the method described in that patent application consists essentially in measuring the reflectance of the object or of the tooth at wavelengths that correspond to sensitivity maxima in the human eye with respect to hue and to saturation, and to deduce from such measurements an indicator for reproducing the transparency of the object, together with a saturation coefficient for the color of the object as seen by the human eye, and the pigmentations of said color relative to white in predetermined wavelength intervals.

It is preferable, particularly when the object is a tooth in the mouth, to use an illuminant which is the standardized diffuse illumination of sunlight, the reflectance of the tooth is measured at wavelengths substantially equal to 440 nm, 495 nm, 520 nm, 577 nm, and 600 nm, and the pigmentations of the color of the object relative to white are determined over wavelength intervals lying respectively between about 400 nm to 550 nm and between about 550 nm and 650 nm.

That method makes it possible to determine the color of a tooth exactly, and then to compare said determined color with known colors of a color chart or palette by comparing the saturation percentage of the tooth color with the corresponding saturation percentages of the colors in the chart or palette, and by comparing the pigmentations of the tooth color with the corresponding pigmentations of the colors of the chart or palette, and finally by comparing the luminance of a white object included in the luminance of the tooth with the luminances of a white object included in the luminances of the colors in the chart or palette.

OBJECTS AND SUMMARY OF THE INVENTION

A particular object of the present invention is to facilitate implementation of that method and its use by dentists or by personnel not specialized in performing colorimetry measurements.

Another object of the invention is to provide a method and apparatus enabling the color of an object that is transparent, diffusing, and absorbent to be determined with great accuracy and without risk of manipulation error.

To this end, the present invention provides a method of determining the color of an object that is transparent, diffusing, and absorbent, in particular such as a tooth in the mouth, the method consisting in illuminating an area of the object by means of a polychromatic light flux, in picking up the light backscattered by the object, and in spectrally analyzing the light picked up, the method consisting in using a diffuse light flux that is substantially uniform and isotropic for illuminating said area of the object, in aiming at a zone within the illuminated area, said zone being of dimensions that are considerably smaller than those of the illuminated area and being approximately centered therein, in forming an image of said zone on spectrum analysis means, and in determining the intensity of the light backscattered by the object at a relatively small number of wavelengths of predetermined values, and corresponding in particular to hue and saturation sensitivity maxima of the human eye.

By illuminating an area of the object that is relatively large compared with the measurement zone, it is possible to avoid edge effects that result from light being diffused and absorbed in the thickness of the object. It is important for the measurement zone not to be subjected to such edge effects which give rise to variations in the color perceived by the human eye or by the detectors of measurement apparatus.

In accordance with the invention, the dimensions of the illuminated area and of the aiming zone on the object satisfy the relationship $d2 \geq d1 + 2\,Dm$ where $d2$ is a dimension or diameter of the illuminated area, $d1$ is a corresponding dimension or diameter of the aiming zone, and $Dm$ is a minimum value of a corresponding dimension of an illumination area for the object as determined experimentally by observation of color variations of the object over a section thereof.

Thus, for a natural tooth, a value $Dm$ has been determined as being equal to about 2 mm.

As a result, the illuminated area of a tooth must have a diameter of not less than 5 mm when the diameter of the aiming zone on the surface of the tooth is about 1 mm.

Furthermore, the invention also provides for the axis of the illuminating light flux and the axis of the optical system picking up the light backscattered by the object to coincide substantially and be perpendicular to the illuminated area of the object.

To facilitate taking of measurements, the invention also provides for the diffuse light flux used for illuminating the object to be circularly symmetrical about its axis.

Measurements are thus independent of the angular position of the measurement means around the axis of the illuminating light flux.

The invention also provides apparatus for determining the color of an object that is transparent, diffusing, and absorbent, in particular such as a tooth in the mouth, the apparatus comprising means for illuminating an area of the object by means of a polychromatic light flux, means for picking up the light backscattered by the object, and means for spectrally analyzing the light picked up, the apparatus comprising a tube having a diffusing inside surface and an open end for pointing at the object to be illuminated, a light source received inside the tube, an optical system disposed inside the tube close to its open end for picking up the light that penetrates into the tube through said end and for forming an image of a small zone of the illuminated area of the object on spectrum analysis means themselves received with the optical system inside a box disposed inside the tube and forming an opaque screen interposed between the light source and the open end of the tube, the tube also being provided with a handle containing power supply and control means for the light source.

Such apparatus makes it possible to illuminate a relatively large area of the object by means of a diffuse light flux that is substantially uniform and isotropic, and to pick up the light backscattered by a very small zone of the illuminated surface of the object, in application of the method as described above. Furthermore, the apparatus is easy to handle and it can be used with one hand only.

According to another characteristic of the invention, the optical system comprises, going from the open end of the tube towards the spectrum analysis means: two achromatic doublets with two filters being interposed therebetween, namely an infrared filter and an ultraviolet filter; followed by a diaphragm on which the image of the illuminated area of the object is formed; a third achromatic doublet receiving the light flux that passes through the diaphragm and generating a beam of substantially parallel rays; and a set of separating plates followed by a mirror disposed obliquely to the axis of the optical system to split said beam of parallel rays into parallel sub-beams that are directed towards the spectrum analysis means.

This optical system has the advantage of not including optical fibers and of avoiding all of the problems that are raised by use of optical fibers (aging, coupling, twisting, curving, transmission, etc.).

According to yet another characteristic of the invention, the spectrum analysis means comprise interference filters each tuned to a determined wavelength and each disposed on the path of one of the above-mentioned sub-beams, together with photodetectors disposed at the outlets of the interference filters.

Advantageously, the tube also contains calibration means comprising a screen of diffusing material or of reference material that receives the light diffused by the inside surface of the tube, together with optical means and spectrum analysis means substantially identical to the above-specified means and receiving the light that is backscattered by said screen.

Finally, the apparatus includes a removable endpiece of transparent material, the endpiece comprising a base for fixing on the open end of the tube and converging sloping fingers whose free ends are designed to be applied against the object to delimit between them said illuminated area of the object, and also serving to delimit a distance between the object and the optical system equal to the focal length of the first lens in said optical system.

This endpiece makes it easier to use the apparatus and it improves the accuracy of the measurements.

BRIEF DESCRIPTION OF THE DRAWINGS

In the following description, given by way of example, reference is made to the accompanying drawings, in which.

MORE DETAILED DESCRIPTION

Figure 1:
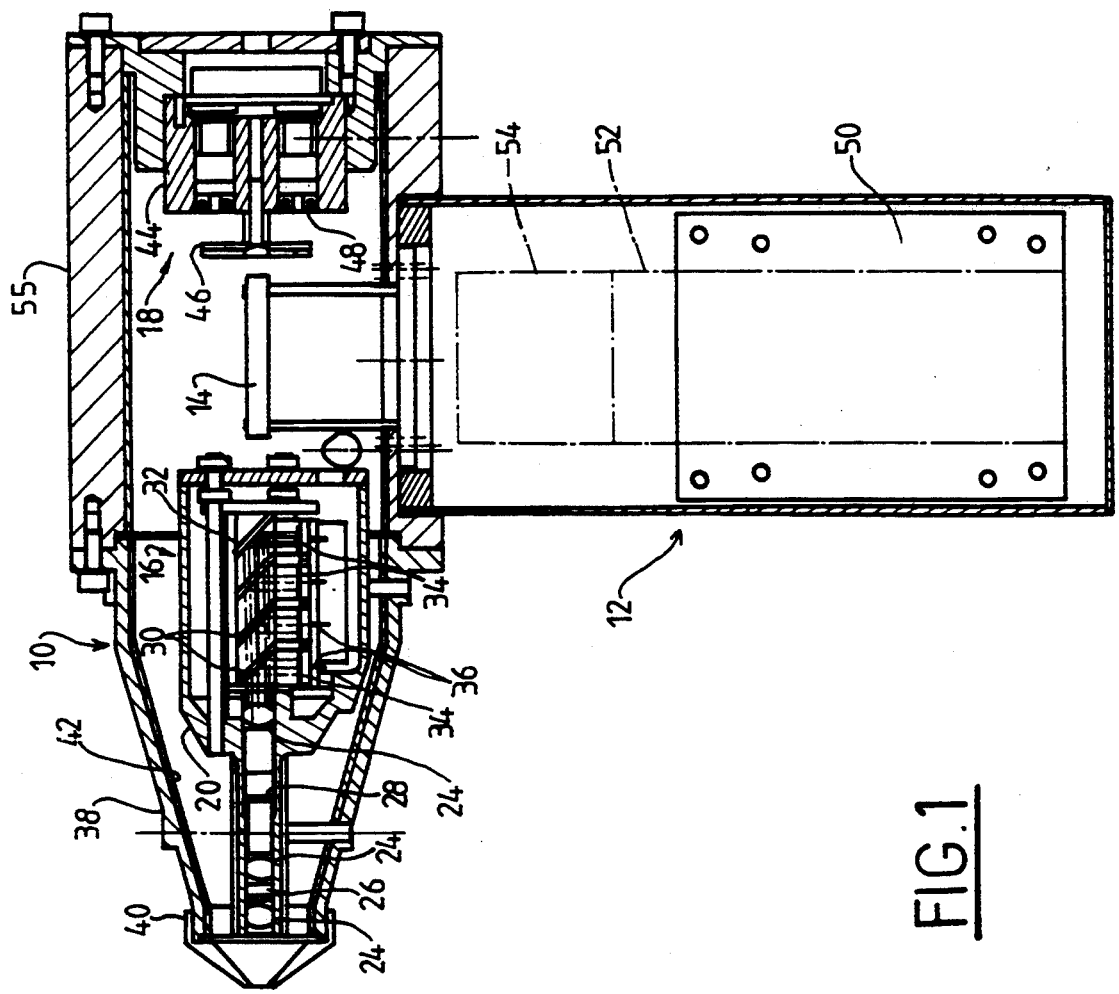
FIG. 1 is a diagrammatic axial section view through apparatus of the invention.

Reference is made initially to FIG. 1 which is a diagram in axial section through one embodiment of apparatus of the invention comprising a box constituted essentially by a tube 10 associated with a handle 12.

The tube 10 contains a light source 14 such as a halogen lamp or a flash lamp, a measurement assembly 16, and a calibration assembly 18. The measurement assembly 16 is housed in the front portion of the tube 10 and comprises a box 20 in which an optical system and means for spectrally analyzing light are housed. The optical system comprises, inside a tube 22 forming the front portion of the box 20, two achromatic doublets 24 between which two filters 26 are disposed, namely an infrared filter and an ultraviolet filter, which filters are followed by a diaphragm 28 whose central orifice is small in size. A third achromatic doublet 24 is disposed behind the diaphragm 28 to generate a beam of substantially parallel rays on a set of three separating plates 30 followed by a mirror 32, the separating plates 30 and the mirror 32 being disposed obliquely relative to the axis of the optical system to split the beam of parallel rays produced by the third achromatic doublet 24 into four sub-beams directed towards four interference filters 34 each tuned to a particular wavelength and each transmitting light to an associated photodetector 36.

This measurement assembly 16 is disposed axially in the tapering front portion 38 of the tube 10 whose open front end receives an endpiece 40 for application against the surface of an object whose color is to be determined.

The dimensions of the endpiece 40 are such that when applied against an object, the object is located at the focus of the first lens in the optical system.

To enable the object to be illuminated by a diffuse light flux that is substantially uniform and isotropic, the lamp 14 is placed on the axis of the tube 10 behind the box 20 of the measurement assembly 16 which thus forms an opaque screen between the lamp and the open front end of the tube 10. In addition, the entire inside surface of the tube 10 has an internal coating 42 of diffusing material, said coating itself being deposited on an underlayer that provides mirror reflection.

The calibration assembly 18 comprises a box 44 received in the rear portion of the tube 10 and closing the rear end of the tube. The box 44 carries a plate 46 disposed behind the lamp 14 inside the tube 10 in such a manner as to ensure that the assembly is illuminated only by the light diffused by the internal coating 42 of the tube 10, the box 44 also including four parallel paths for picking up and spectrally analyzing the light backscattered by the plate 46, each path comprising a diaphragm 48, a pair of filters, one ultraviolet and the other infrared, an interference filter tuned to the same wavelength as one of the filters 34 in the measurement assembly 16, and a photodetector receiving the light transmitted by said interference filter. The photodetectors of the calibration assembly 18, like the photodetectors 36 of the measurement assembly 16 being mounted on an electronics card that performs preamplification.

The plate 46 may be made of the same material as the coating 42, or it may be made of a standard reference material.

The handle 12 of the apparatus contains a card 50 having a microprocessor for processing the signals output by the photodetectors of the measurement assembly 16 and of the calibration assembly 18, together with rechargeable batteries 52 and a power supply 54 for the lamp 14.

In addition, the apparatus further includes a display screen and a control keypad that are mounted, for example, at 55 on the top face of the tube 10 and/or on the handle 12.

The apparatus operates as follows:

The endpiece 40 mounted at the front end of the tube 10 is applied to the surface of an object whose color is to be determined. By controlling the lamp 14, a light flux or flash is produced inside the tube 10 and is transformed into a diffuse light flux that is substantially uniform and isotropic which is guided towards the surface of the object by the tapering front portion 38 of the tube.

The light backscattered by the object is picked up by the optical system of the measurement assembly 16, with the diameters and the focal lengths of the lenses in the first achromatic doublet 24 being such that the optical system picks up backscattered light only and does not pick up light that is specularly reflected by the surface of the object. To do this, the ratio $\phi/f$ of the diameter $\phi$ over the focal length f of the first lens must be less than a value of about 0.45. The image of the surface of the object is re-formed on the diaphragm 28 by the achromatic doublet 24 with a magnification equal to 1. The central orifice of the diaphragm 28 is of small diameter, about 1 mm when determining the color of a tooth. The diaphragm is substantially at the focal point of the third achromatic doublet 24, which thus transforms the light flux from said diaphragm into a beam of substantially parallel rays that is split up by the separating plates 30 and the mirror 32 into parallel subbeams directed towards the interference filters 34. The output signals from the photodetectors 36 located behind said interference filters thus represent the intensities of the light backscattered by the object at the wavelengths to which the interference filters are tuned. As mentioned in the above-specified prior patent application filed by the Applicant, these wavelengths correspond to hue and saturation sensitivity maxima of the human eye and are preferably equal to 440 nm, 495 nm, 520 nm, and 590 nm.

Simultaneously, the light diffused by the internal coating of the tube 10 illuminates the plate 46 and the light backscattered by said plate is spectrally analyzed at the same wavelengths as the light backscattered by the object whose color is to be determined.

The output signals from the photodetectors in the measurement assembly 16 and in the calibration assembly 18 are preamplified and are then processed by the microprocessor card 50 so as to deliver the spectral components of the light backscattered by the object at the above-specified wavelengths.

The output signals from the photodetectors in the calibration assembly 18 are taken into account so as to provide measurements that are independent of variations in the power of the lamp 14, of temperature drift, etc., and that can additionally be automatically calibrated relative to a standard reference material assuming that the plate 46 is made of a reference material whose colorimetric characteristics are known accurately.

The results of the measurements are displayed on the display screen fitted to the apparatus.

When measurements are performed on objects that are transparent, diffusing, and absorbent, it is important to satisfy certain conditions in order to ensure that the measurements are accurate.

Figure 2:
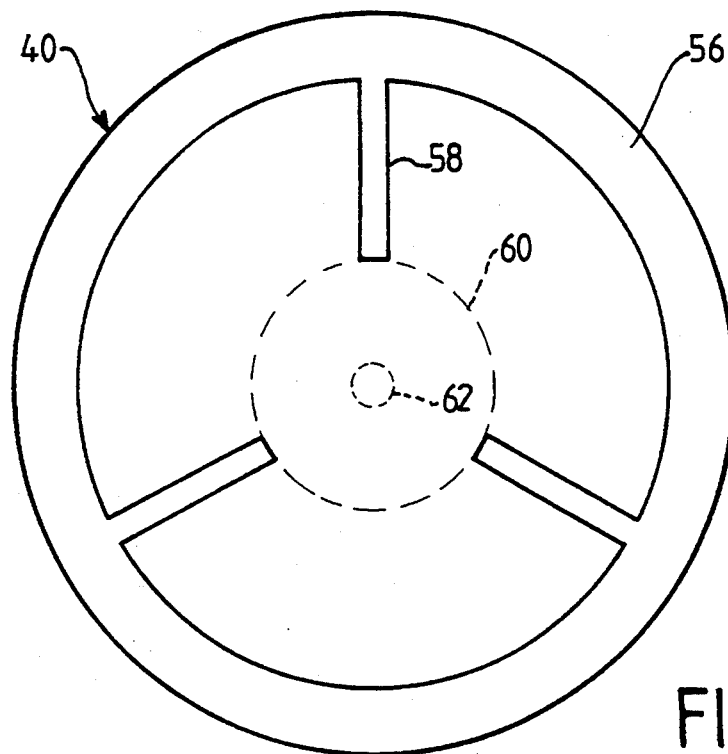
FIG. 2 is a front view on a larger scale of the endpiece of the apparatus.

The endpiece 40 fitted to the apparatus of the invention and shown on a larger scale in FIG. 2 serves to ensure that some of these conditions are satisfied.

Figure 3:
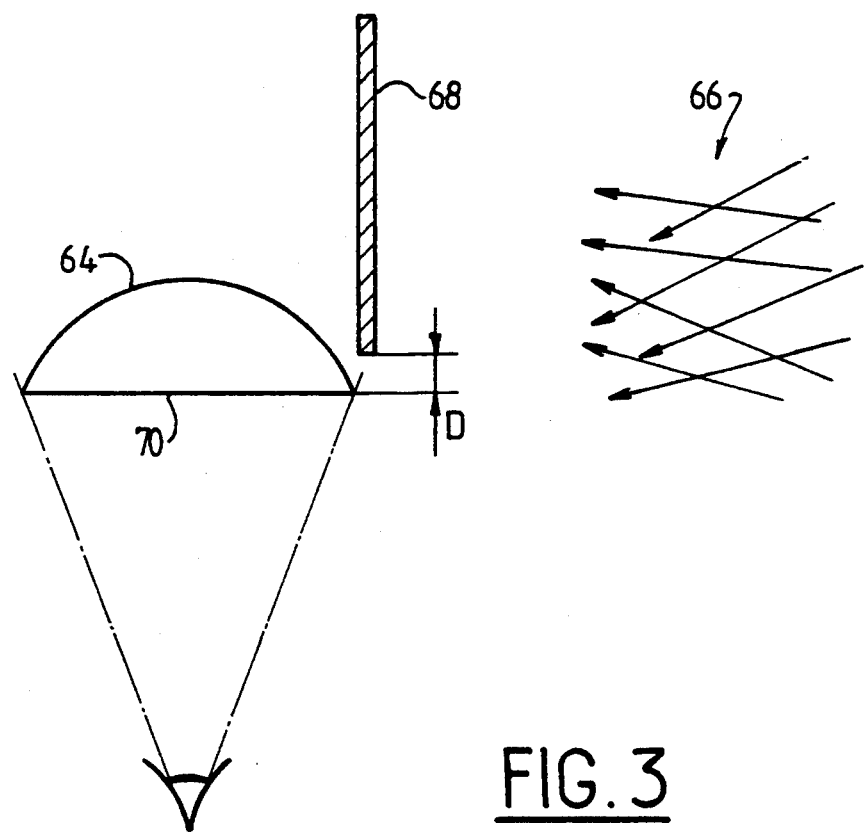
FIG. 3 is a diagram showing the method used for experimentally determining the minimum dimensions for the area of an object that is illuminated.

The endpiece 40 is made of transparent material and comprises a cylindrical base 56 for fixing on the open front end of the tube 10, and three fingers 58 disposed at 120° intervals from one another and sloping forwards to converge substantially on the axis of the endpiece 40, delimiting, between their free ends, a circle 60 which defines the illuminated area of the object. The aiming zone of the optical system of the measurement assembly 16 is represented in FIG. 2 by a circle 62 whose diameter corresponds to the diameter of the central orifice in the diaphragm 28. The diameter of the circle 62 is about 1 mm. In order to ensure that the measurements are accurate, and in particular that the aiming zone 62 is not subject to the edge effects that result from light being diffused and absorbed inside the object, the illuminated area 60 must be considerably greater in diameter than the aiming zone 62, and this is defined by the following relationship:

$$d2 \geq d1 + 2Dm$$

where d2 is the diameter of the illuminated area 60, d1 is the diameter of the aiming zone 62, and Dm is a minimum diameter value for an illuminated area of the object, with said minimum diameter being determined experimentally in the manner described below with reference to FIG. 3.

The procedure is as follows, in particular for a tooth (FIG. 3):

A natural tooth 64 is cut longitudinally or axially and the outside surface of the tooth is illuminated by diffuse light flux 66, an opaque screen 68 is interposed between the outside surface of the tooth and the light flux 66, said screen extending perpendicularly to the plane of the sectioned face 70 of the tooth and its leading edge being at a distance D from said plane, and the sectioned face 70 of the tooth is watched to observe variations in its color as the distance D is varied by displacing the screen 68. Under such circumstances, it is found that there exists a limit value Dm for D such that:

if D varies through values less than Dm, then color variations are observed on the sectioned face 70 of the tooth; whereas if D varies through values greater than Dm, then such color variations are not observed on the sectioned face 70 of the tooth. In other words, increasing the illuminated area of the tooth no longer has any effect on the color of the sectioned face of the tooth, which means that said color is no longer modifiable by light diffusing through the tooth and by edge effects of the illuminated area.

For a natural tooth, this minimum value Dm is about 2 mm.

Using the above-specified relationship, the diameter of the illuminated area 60 of the object is determined on the basis of the selected diameter for the observed zone 62.

With a tooth, when the diameter of the observed zone 62 is about 1 mm, a value of 5 mm is obtained for the minimum diameter of the illuminated area 60.

When the above-mentioned minimum value Dm is to be determined experimentally for a family of objects in which transparency may vary from one object to another, the experiment should be performed on the most transparent object of the family.

Furthermore, it is advantageous, in order to facilitate measurement, for the inside surface of the front portion of the tube 10 which forms the structure guiding the illuminating flux to the object to be circularly symmetrical about its axis, and for the optical system that picks up the light backscattered by the object to be coaxial with said inside surface. The lamp 14 and the calibration assembly 18 are likewise disposed on the axis of the tube 10.

The lamp 14 may be a halogen lamp or a flash lamp or a discharge lamp and it preferably emits light flux that is approximately equi-energy over the visible spectrum.

In general, the invention makes it possible accurately to determine the color of an object that is transparent, diffusing, and absorbent, and it is particularly suitable for use in making dental prosthesis.

We claim:

1. A method of determining the color of an object that is transparent, diffusing, and absorbent, the method comprising illuminating an area of the object with a diffuse polychromatic light flux that is substantially uniform and isotropic, picking up light backscattered by the object from an aiming zone within the illuminated area, said zone being of dimensions that are considerably smaller than those of the illuminated area and being approximately centered therein, forming an image of said zone on a spectrum analysis device and determining by spectral analysis with said device the intensity of the light backscattered by the object at a relatively small number of wavelengths of predetermined values, and corresponding to hue and saturation sensitivity maxima of the human eye.

2. A method according to claim 1, wherein the dimensions of the illuminated area and of the aiming zone satisfy the following relationship $d2 \geq d1 + 2 Dm$, where $d2$ is a dimension or a diameter of the illuminated area, $d1$ is a corresponding dimension or diameter of the aiming zone, and Dm is a minimum value characteristic of the object, Dm being determined experimentally by observing variations in color on a section thereof as a function of variations in the size of the illuminated area of the object.

3. A method according to claim 2, wherein for determining the colors of objects of the same kind, the above-specified value Dm is determined experimentally on the most transparent one of the objects.

4. A method according to claim 2, wherein the above-specified value Dm is about 2 mm.

5. A method according to claim 2, wherein the diameter $d1$ of the aiming zone is about 1 mm.

6. A method according to claim 1, wherein the illuminating diffuse light flux is circularly symmetrical about its axis.

7. A method according to claim 1, wherein the axis of the illuminating light flux and the axis of the optical system picking up the light backscattered by the object coincide substantially and are perpendicular to the illuminated area of the object.

8. A method according to claim 1, wherein the object is a tooth.

9. Apparatus for determining the color of an object that is transparent, diffusing, and absorbent, the apparatus comprising a tube having a diffusing inside surface and an open end for pointing at the object, a light source received inside the tube for illuminating an area of the object by means of a diffuse polychromatic light flux that is substantially uniform and isotropic, an optical system disposed inside the tube close to its open end for picking up the light that penetrates into the tube through said end and for forming an image of a small zone of the illuminated area of the object on spectrum analysis means themselves received with the optical system inside a box disposed inside the tube and forming an opaque screen interposed between the light source and the open end of the tube, the tube also being provided with a handle containing power supply and control means for the light source.

10. Apparatus according to claims 9, wherein the optical system comprises, going from the open end of the tube towards the spectrum analysis means: two achromatic doublets with two filters being interposed therebetween, namely an infrared filter and an ultraviolet filter; followed by a diaphragm on which the image of the illuminated area of the object is formed; a third achromatic doublet receiving the light flux that passes through the diaphragm and generating a beam of substantially parallel rays; and a set of separating plates followed by a mirror disposed obliquely to the axis of the optical system to split said beam of parallel rays into parallel sub-beams that are directed towards the spectrum analysis means.

11. Apparatus according to claim 10, wherein the spectrum analysis means comprise interference filters each tuned to a predetermined wavelength and each disposed on the path of one of the above-mentioned sub-beams, together with photodetectors disposed at the outlets of the interference filters.

12. Apparatus according to claim 9, wherein the tube also contains calibration means comprising a screen of diffusing material or of reference material that receives the light diffused by the inside surface of the tube, together with optical means and spectrum analysis means substantially identical to the above-specified means and receiving the light that is backscattered by said screen.

13. Apparatus according to claim 9, including circuits for amplifying and processing the output signals from the spectrum analysis means.

14. Apparatus according to claim 9, wherein the above-specified optical system is coaxial with the open end of the tube.

15. Apparatus according to claim 9, wherein the inside surface of the tube is circularly symmetrical about its axis, the light source being disposed on the axis of symmetry of said inside surface.

16. Apparatus according to claim 9, including a removable endpiece of transparent material, the endpiece comprising a base for fixing on the open end of the tube and converging sloping fingers whose free ends are designed to be applied against the object to delimit between them said illuminated area of the object, and also serving to delimit a distance between the object and the optical system equal to the focal length of the first lens in said optical system.

17. Apparatus according to claim 9, wherein the first lens of the optical system has a diameter $\phi$ and a focal length f that are determined so that their ratio $\phi$f is less than a predetermined value, thereby preventing the optical system from picking up light that is specularly reflected by the object.

18. Apparatus according to claims 9, wherein the object is a tooth.

* * * * *